(12) United States Patent
Peterson (10) Patent No.: US 6,197,002 B1
(45) Date of Patent: *Mar. 6, 2001

(54) LAPAROSCOPIC TOOL AND METHOD (75) Inventor: Francis Peterson, Prescott, WI (US)

(73) Assignee: Phillips Plastics Corporation, Phillips, WI (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/246,228

(22) Filed: Feb. 8, 1999

Related U.S. Application Data (63) Continuation-in-part of application No. 08/988,157, filed on Dec. 12, 1997, now Pat. No. 6,004,303.

(51) Int. Cl.[7] .................................................. A61M 5/178
(52) U.S. Cl. ................................ 604/164.01; 604/167.01; 604/264
(58) Field of Search .................................... 604/174, 117, 604/264, 164, 278, 164.01, 164.02, 167.01, 167.02, 167.03, 167.06, 246, 272, 280, 256

(56) References Cited

U.S. PATENT DOCUMENTS

| 4,760,933 | 8/1988 | Christner et al. . | |
|---|---|---|---|
| 4,828,554 | 5/1989 | Griffin . | |
| 5,127,626 | 7/1992 | Hilal et al. . | |
| 5,158,533 | 10/1992 | Berry et al. . | |
| 5,330,437 | 7/1994 | Durman . | |
| 5,364,372 | 11/1994 | Danks et al. . | |
| 5,380,292 | 1/1995 | Wilson . | |
| 5,538,509 | 7/1996 | Dunlap et al. . | |
| 5,545,150 | 8/1996 | Danks et al. . | |
| 5,580,344 | 12/1996 | Hasson . | |
| 5,634,911 | 6/1997 | Hermann et al. . | |
| 5,634,937 | 6/1997 | Mollenauer et al. . | |
| 5,662,615 | * 9/1997 | Blake, III ............................. | 604/167 |
| 5,720,730 | 2/1998 | Blake, III . | |
| 5,746,720 | * 5/1998 | Stouder, Jr. .......................... | 604/117 |
| 5,882,344 | * 3/1999 | Stouder, Jr. .......................... | 604/264 |
| 5,957,888 | * 9/1999 | Hinchliffe ............................ | 604/117 |
| 6,004,303 | * 12/1999 | Peterson .............................. | 604/264 |

FOREIGN PATENT DOCUMENTS 94 22357  10/1994  (WO) .
98 36785   8/1998  (WO) .

* cited by examiner

Primary Examiner—Sharon Kennedy
Assistant Examiner—Michael J Hayes
(74) Attorney, Agent, or Firm—Crawford PLLC (57) ABSTRACT The present invention is directed to an apparatus for use in internal surgical procedures and is particularly advantageous for use in laparoscopic surgical procedures. An example implementation is directed to a tool having a depth-adjustable cannula having an upper portion that rests on the body, and having an automatically-sealing channel that readily accepts the insertion and removal of surgical instruments without permitting gases to pass. In one particular embodiment, the tool includes a low-profile platform for stabilizing the tool on a body layer, a projection channel with a flexible sleeve for maintaining the channel closed, and an adjustable member for setting the penetration depth of the tool. The flexible sleeve is sufficiently elastic to close the inner channel in response to pressurization between the outside of the flexible sleeve and the inner surface of the hollow channel. The low-profile platform and the adjustable member permit use of the same tool for different body-wall thicknesses.

21 Claims, 6 Drawing Sheets

LAPAROSCOPIC TOOL AND METHOD

RELATED PATENT DOCUMENTS

This application is a continuation-in-part application of U.S. patent application entitled, "Choker-Catheter," Ser. No. 08/988,157, filed on Dec. 12, 1997 (PHIL.109US01), now U.S. Pat. No. 6,004,303, issued Dec. 21, 1999, and assigned to the instant assignee and incorporated herein in its entirety.

FIELD OF THE INVENTION

The present invention relates to an apparatus for use in laparoscopic surgery and, more particularly, to an apparatus for providing a seal or valve structure within a cannula which effectively and cost efficiently prevents inert gas from escaping while allowing the repeated insertion and removal of surgical instruments through the cannula.

BACKGROUND OF THE INVENTION

Recent advancements in surgical techniques and instruments have permitted for incisions of reduced size for a variety of surgical procedures. For example, surgical procedures which only a few years ago required an incision six or seven inches in length are today performed through incisions requiring less than one inch in length. Among other advancements, one type of surgical instrument that has been significant in this regard is the trocar.

In general, a trocar is a sharply pointed surgical tool that is used to create and maintain small, bowl-like incisions in a body cavity. Surgical instruments, including miniaturized optical devices, can be inserted through these small incisions and manipulated to perform surgical procedures within the body cavity without ever exposing the patient's internal organs or structures to the outside environment. By enabling the creation and maintenance of small working holes within a patient's body wall, conventional trocars have greatly contributed to the reduction and size of the incisions required to perform surgical procedures thereby reducing the related complications.

Conventional trocars generally include an obturator and a cannula. An obturator is a small, nail-like structure for penetrating the body wall to create a working channel into the body cavity. The cannula is a tube-like structure which is inserted into the incision made by the obturator to maintain a working channel even after the obturator is removed. In a typical scenario, the obturator and cannula are assembled into a single unit by inserting the obturator within the cannula, and then a combination is used to puncture the body wall. The obturator can then be carefully withdrawn from the cannula without removing the cannula from the body wall. Surgical instruments can be inserted through this cannula to perform an entire surgical procedure within the body cavity.

In many surgical procedures involving trocars, the body cavity is inflated with a nontoxic gas before the trocar is employed to create a working pocket or volume within the patient and to prevent the trocar from penetrating internal organs during insertion. In an appendectomy procedure, for example, a patient's abdomen is inflated with a gas through a veress needle. The obturator is then used to place cannulas in various locations throughout the inflated abdomen to perform the procedure. One such cannula would typically be used to pass a small camera and light into the body cavity so the surgeon could view the operating area within the patient. Other cannulas would be used at other locations to pass surgical instruments into the cavity and remove tissue such as the appendix from the patient.

Maintaining the patient's abdomen in an inflated state throughout this procedure is important. To this end, cannulas are often provided with sealing flap valves that are arranged to prevent gas from escaping from the patient's abdomen after the obturator has been withdrawn. These sealing valves, however, do not prevent gas leakage when the surgical instrument has a diameter that is smaller than the diameter of the cannula seal. Instead gas can easily pass through the gap between the inner walls of the cannula and the outer surface of the surgical instrument to deflate the work area. To prevent such deflation of this type from occurring, physicians often are required to utilize only those instruments whose dimensions closely match those of the cannula. This requirement apparently limits the surgeon's freedom of choice in selecting surgical instruments for the procedure. Thus, while a surgeon's instrument might be preferred by a physician, the physician might nonetheless be forced to use a less preferred, and possibly less effective, tool to perform a procedure to avoid deflating a body cavity.

It is also important for the surgeon to use an assembled obturator and cannula for the particular operation and/or patient. Depending on the body cavity to be explored and the patient undergoing the surgery, the surgical procedures can vary significantly. For example, using an assembled obturator and cannula to puncture the stomach of a baby is quite different than using an assembled obturator and cannula to puncture the stomach of an obese adult. Typically, the procedure for a baby requires that the assembled obturator and cannula be inserted just a short way, enough to pierce a thin stomach wall. Conversely, the same procedure for an obese adult requires that the assembled obturator and cannula be inserted through a relatively thick stomach wall. For such procedures, the conventional obturator and cannula assembly is often too long or too short, thereby making the surgery awkward. For example, when using an obturator and cannula assembly that is too long, the upper end of the assembly extends far above the stomach wall thereby making the assembly unstable.

Accordingly, there is a need for a surgical instrument and procedure that addresses the above-mentioned, and other, problems in the prior art.

SUMMARY OF THE INVENTION

The present invention is directed to an apparatus or tool for use in internal surgical procedures and, more particularly, to a laparoscopic tool for surgical procedures. In a more specific example embodiment, the tool includes a low-profile platform for stabilizing the tool on a body layer, a collapsing sleeve in a projection channel within the tool for maintaining the channel closed, and an adjustable member for setting the penetration depth of the tool.

In another example embodiment, an apparatus is used for inserting through a body layer and into a body cavity for surgical procedures. The apparatus includes: an elongated tube including an entry port, a channel and an extended portion configured and arranged to extend the entry port above the body layer; and a flexible sleeve located within the hollow channel of the tube and being supported via the elongated tube at first and second locations of the elongated tube, wherein the flexible sleeve is configured and arranged to have slack between the first and second locations such that the sleeve is compressed when under pressure while in use to close the opening.

In another particular embodiment, a method for accessing through a body layer and into a body cavity for surgical procedures, comprises: providing a tool including an entry port, a channel and an extended portion configured and arranged to extend the entry port above the body layer, and providing a flexible sleeve within the hollow channel; inserting the tool into the body and setting the extended portion on the body layer; placing an instrument within the channel and within the flexible sleeve; permitting the flexible sleeve to conform around the instrument while the instrument is within the channel, and permitting the flexible sleeve to close upon itself while no object is within the channel, such that the flexible sleeve includes sufficient slack between the first and second locations that the sleeve responds as such when under pressure.

Another example implementation is directed to a tool having a depth-adjustable cannula having an upper portion that rests on the body, and having an automatically-sealing channel that readily accepts the insertion and removal of surgical instruments without permitting gases to pass through a channel in the cannula.

The above summary of the present invention is not intended to describe each illustrated embodiment of the present invention. Other aspects and embodiments of the invention will become apparent upon a review of the figures and detailed description.

BRIEF DESCRIPTION OF THE DRAWINGS

The invention may be more completely understood in consideration of the detailed description of various embodiments of the invention which follow in connection with the accompanying drawings, in which.

While the invention is amenable to other various modifications in alternative forms, specifics thereof have been shown by way of example in the drawings and will be described in detail. It should be understood, however, that the intention is not to limit the invention to a particular embodiment described. On the contrary, the intention is to cover all modifications, equivalents, and alternatives falling within the spirit and scope of the invention as defined by the appended claims.

DETAILED DESCRIPTION

The present invention is applicable to a variety of apparatus and arrangements in which external instruments are to be passed through an opening separating two environments in which a pressure difference between these environments exists and in which maintaining a seal between these environments is beneficial. The invention has been found to be particularly advantageous in laparoscopic surgery where surgical instruments are passed into a body cavity (human or otherwise) to perform an operation. While the present invention is not so necessarily limited, various aspects of the invention can be appreciated through discussion of application examples in such an environment.

Figure 1A:
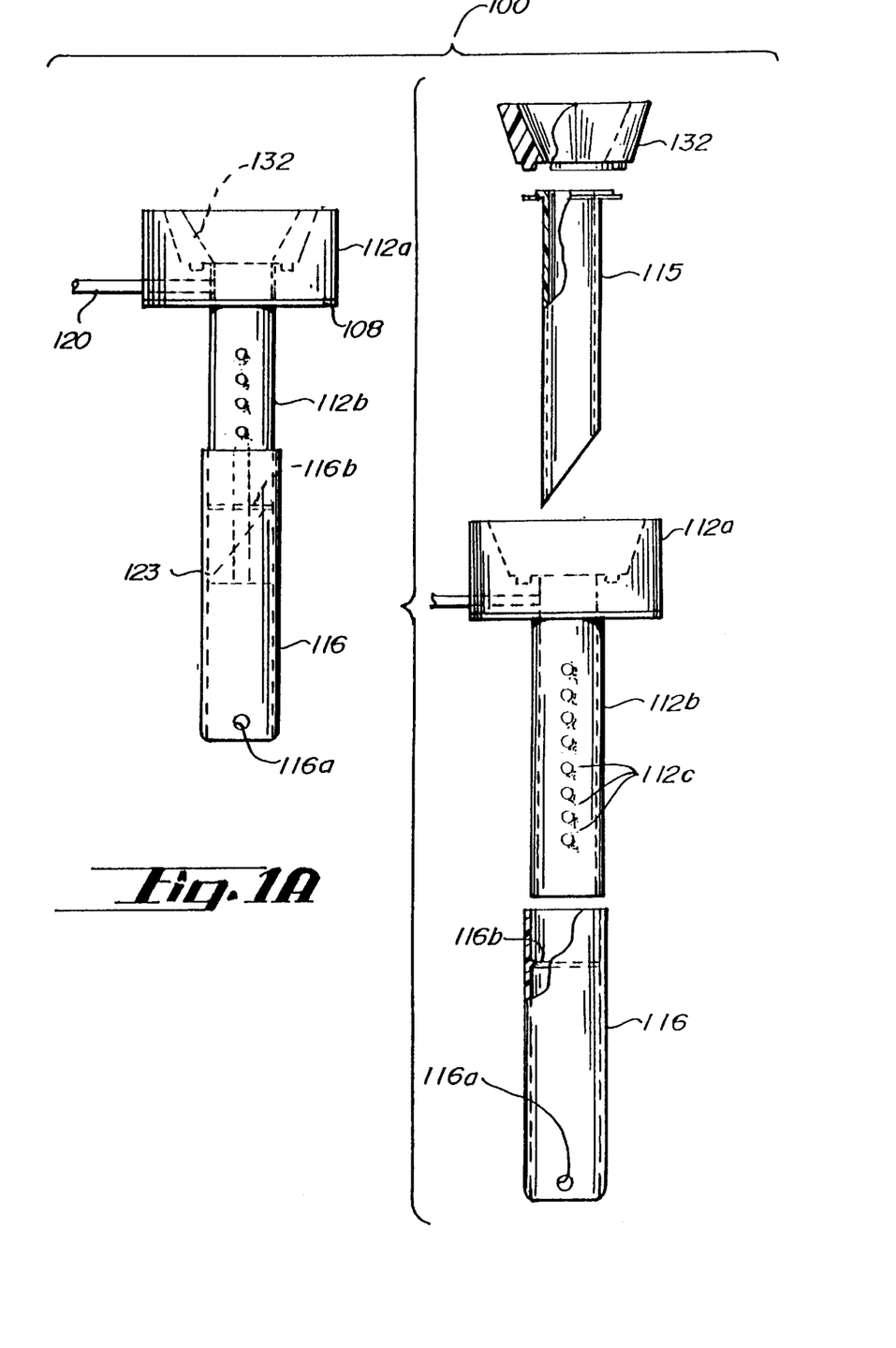
FIG. 1A is a perspective view of an example surgical tool, according to the present invention, with a body-piercing portion of the tool removed.

Turning now to the drawings, FIGS. 1A–1E illustrate an example laparoscopic tool 100 that is used to create and maintain a small incision through a body layer, such as a stomach wall, having any of a number of thicknesses. FIG. 1A shows the tool 100 from a side view with the piercing portion of the tool 100 removed. The laparoscopic tool 100 includes a main body 112 including an upper portion 112a and an elongated section 112b having a hollow center channel, an inner flexible tube 115 for collapsing the channel sealed, and an outer adjustment sleeve 116 adapted to provide a depth-settable scope at the bottom of the tool 100. The inner flexible tube 115 is open-ended at each end and fits within the channel of the elongated section 112b. The inner flexible tube 115 has one end secured between a tube lock 132 and the upper portion 112a, and has another end secured at a location 123 near the end of the elongated section 112b, for example, using a heat weld, glue or other adhering substance. The inner flexible tube 115 has sufficient slack so that it collapses closed under a pressure in the body cavity, for example, as provided into the body cavity via a gas supply feeding a channel 120.

Figure 1B:
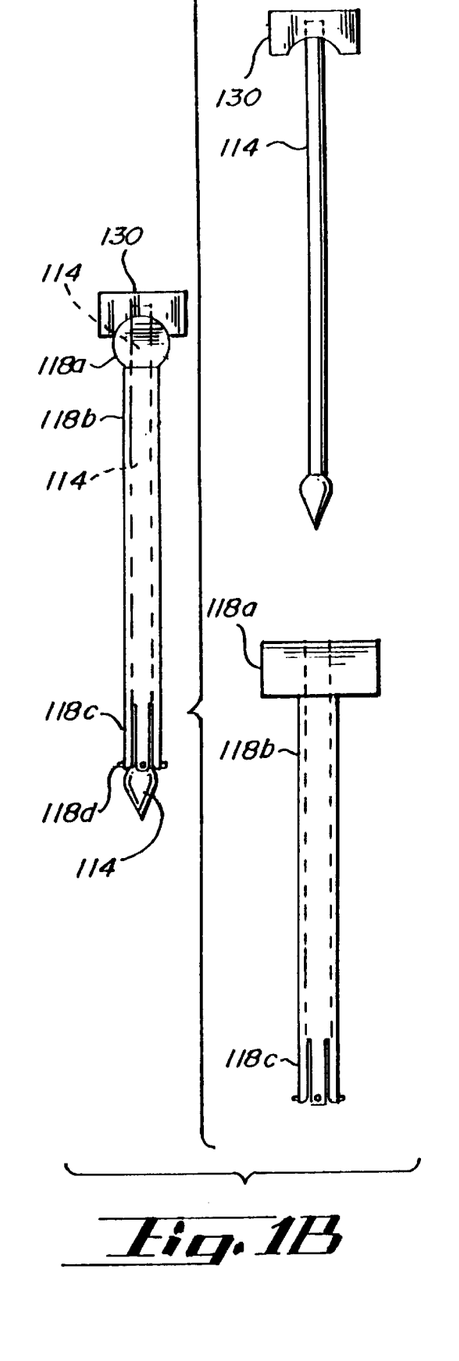
FIG. 1B is a perspective view of the body-piercing portion of the example surgical tool of FIG. 1A, according to the present invention.

FIG. 1B shows the piercing portion of the tool 100 of FIG. 1A. This portion of the tool 100 includes a pin 114 secured at an upper end to a pin holder 130, and a lock 118. The lock 118 has a lock head 118a, a pin-receiving channel 118b, and a separable end 118c. The separable end 118c includes a plurality of sections (e.g., 3 or 4), each having an outwardly-extending protrusion 118d that is designed to lock into a corresponding aperture 116a within the outer adjustment sleeve 116 of FIG. 1A.

Figure 1C:
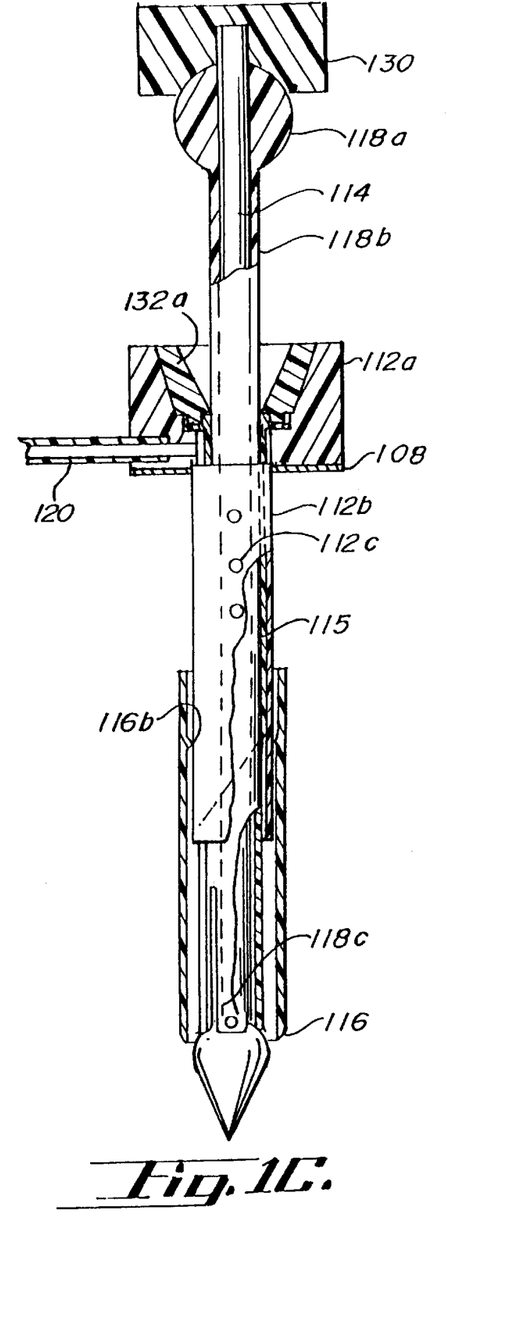
FIG. 1C is a cross-sectional side-end view of the example surgical tool of FIGS. 1A and 1B, according to the present invention, shown in assembled form.

As shown in the cross-sectional view of FIG. 1C, the piercing portion (FIG. 1B) of the tool 100 is inserted into the inner flexible tube 115 within the channel of the elongated section 112b. Once assembled, the piercing portion (FIG. 1B) of the tool 100 can be adjusted along the elongated section 112b so that the distance between the underside of the upper portion 112a and the girth at the bottom of the pin 114 corresponds to the thickness of the body layer being penetrated. With the piercing portion of the tool 100 adjusted for the corresponding body layer thickness, the upper portion 112a can rest on the body layer and thereby provide a foundation above the fatty body layer for insertion and control of instruments to be inserted through (into and out of) the inner flexible tube 15. The entry port, beginning at the upper side of the upper portion 132a, has a conical shape to aid in guiding instruments into the inner flexible tube 115.

The above example embodiment of the present invention is advantageous in that only one laparoscopic tool is needed for a variety of body layer thicknesses. The above embodiment is also advantageous in that the upper portion 112a of the main body 112 extends above the body layer. This provides the operator (or surgeon) a wide and elevated base, or platform, over the outer body layer and from which the operator can control the surgical instruments. In one embodiment, the upper portion 112a is about ¾ inch high and several inches wide; however, the height and girth of the upper portion 112a can vary.

Figures 1D, 1E:
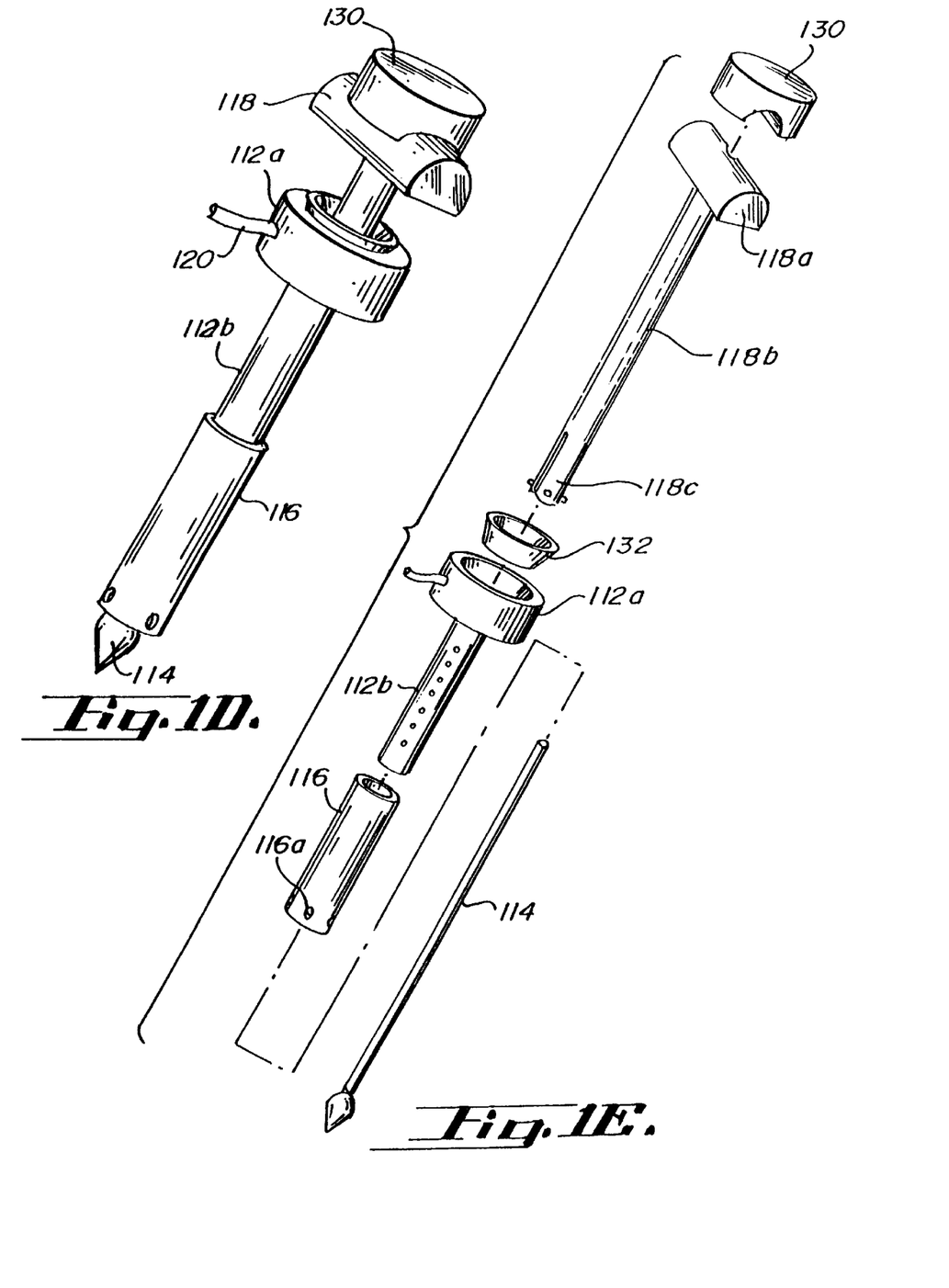
FIG. 1D is a perspective view of the example surgical tool of FIGS. 1A and 1B, according to the present invention, shown in assembled form.
FIG. 1E is a perspective view of the example surgical tool of FIG. 1A, according to the present invention, shown in unassembled form.

FIGS. 1D and 1E respectively illustrate perspective views of the tool 100 of FIG. 1A in assembled and unassembled form.

Referring now to FIGS. 1C–1D, the pin holder 130 includes a curved surface that mates with a curved surface on the lock head 118a. When the pin holder 130 is turned relative to the lock head 118a so that the two surfaces are in a locked and non-mated position, these curved surfaces provide a cam action to draw the bulb end of the pin 114 part way into the end of the lock 118. This cam action, in turn, causes the flexible end 118c of the lock 118 to lock into the end 116a of the sleeve 116, thereby setting the various parts of the laparoscopic tool 100 so that it can be used to make the desired incision. Once the incision is made, the gas supply can be used to inflate the inner flexible tube 115 and body cavity, and the pin holder 130 can be turned relative to the lock head 118a so that the two surfaces are in a mated position. Turning the pin holder 130 in this manner causes the flexible end 118c of the lock 118 to be released from its lock into the end 116a of the sleeve 116. The lock head 118a is then drawn upward and out of the main body 112 to remove the lock 118 and the pin/pin-holder assembly 114/130 from the main body 112. Surgical instruments are then inserted into the tube lock 132 and the end of the inner flexible tube 115 for viewing and/or surgical manipulations within the inflated cavity.

Another important aspect of the present invention concerns maintaining that the body cavity is in an inflated state throughout the procedure. To this end, the inner flexible tube 115 is configured and arranged to seal the incision during the surgery, even after the pin 114 is withdrawn and other instruments are inserted and withdrawn. Regardless of the diameters of the instruments, gas cannot easily pass into or out of the body cavity and deflate the work area. In various embodiments, the inner flexible tube 115 is constructed of a slippery polyurethane or Teflon-like material to permit the easy passage of an external instrument through the sleeve to exit the main body 112 at its upper end. The slippery, plastic, polyurethane-like material also provides the required elasticity to allow the flexible tube to be compressed under pressure to close the opening of the inner channel formed within the flexible tube.

When used for laparoscopic surgery, the tool 100 creates a small hole within the body cavity, with the hole sized to match the outer diameter of the outer adjustment sleeve 116. The body cavity is generally pressurized using an inert gas, such as $CO_2$, such that the internal pressure within the body cavity is greater than the outside air. When the outer adjustment sleeve 116 is inserted within the pressurized body cavity, this pressurization enters the outer adjustment sleeve 116 at its lower end and thereby compresses the inner flexible tube 115. Because the flexible tube 115 is attached at the end of the main body 112, the flexible tube 115 gathers and compresses, closing the channel along the whole length of the flexible tube 115 and preventing the escape of the pressurized gas from inside the body cavity.

When in this configuration, a surgical instrument can be inserted through tube lock 132 to enter within the inner channel of the now collapsed inner flexible tube 115. As the instrument is inserted through the flexible tube, the flexible tube will conform around the external instrument, thus permitting the instrument to pass through the inner flexible tube 115 and exit the rigid main body 112. At the same time, the pressurization is present within the main body's upper end. The pressurization continues to press the flexible tube against the surfaces of the external instrument as it passes through the inner channel. The external instrument can now be used to perform surgical procedures within the body cavity.

As the external instrument is removed, it passes back through the inner channel of the flexible tube. Pressurization from within the body cavity maintains the collapsed structure of the flexible tube, thereby maintaining the seal of the inner channel around the instrument until it is closed when the instrument is completely removed.

In accordance with one aspect of the present invention, an example surgical procedure includes using the laparoscopic tool 100 in assembled form (FIG. 1D) to puncture an incision through a body wall. This procedure includes setting the outer adjustment sleeve 116 so that it is ratched all the way up along the elongated section 112b toward the upper portion 112a. In one implementation, the outer adjustment sleeve 116 includes an encircling ridge 116b for catching and locking onto the protrusions 112c of the elongated section 112b. The puncture is then performed by pressing the tool 100 into the body until the underside of the upper portion 112a resides on the skin or outer body layer. In one example application, the underside of the upper portion 112a is adhered to the stomach wall using two-way tape 108. Next, with the main body 112 held against the skin, the lock 118 is pressed downward. This causes the outer adjustment sleeve 116 to ratchet with the pin further into the body cavity, then to the desired depth. In one application, the position of the outer adjustment sleeve 116 is selected for a desired depth (e.g., up to 3–4½ inches below the main body 112), depending on the thickness of the body layer (e.g., body fat) from the outer skin or layer to where the incision reaches the body cavity. Once the incision is complete, the pin 114 and the lock 118 are unlocked and removed to permit a surgical instrument to be inserted into the inflated body area for viewing and manipulation.

Figures 2A, 2B, 2C, 2D, 2E, 2F:
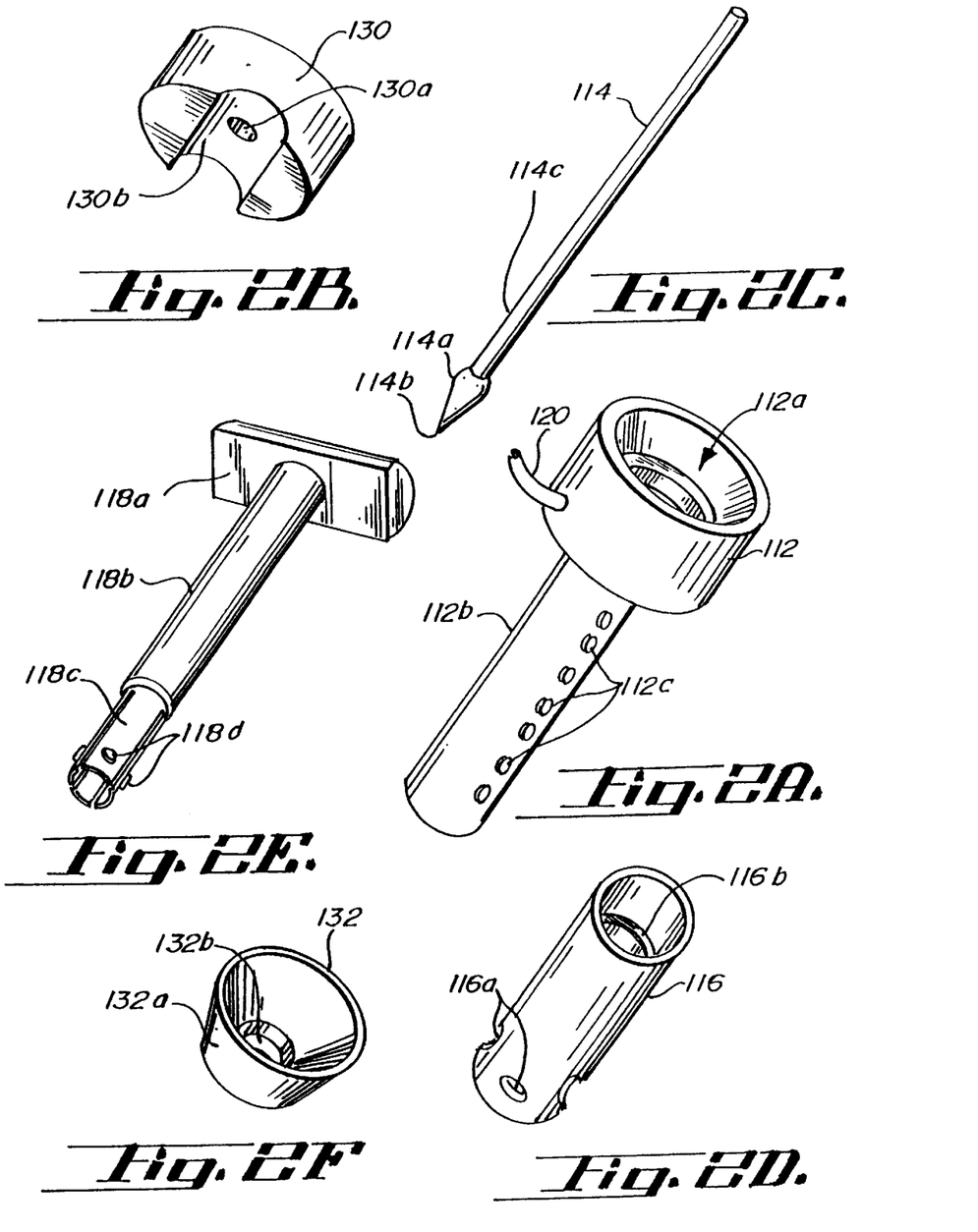
FIGS. 2A–2F are perspective views of various portions of an example surgical tool manufactured in a manner consistent with the example surgical tool of FIGS. 1A, 1B and 1C, also according to the present invention.

FIGS. 2A–2F show perspective views of example parts used for implementing the surgical tool 100 of FIGS. 1A, 1B and 1C. In FIG. 2A, the upper portion 112a of the main body 112 is shown to include a recess area for receiving and securing therein an end of the flexible tube (115 of FIG. 1A) with the tube lock (132 of FIG. 2F) over the end of the flexible tube.

The main body 112 further includes protrusions 112c along its extended portion for engaging and locking to an encircling ridge 116b on the inner surface of the sleeve 116 (FIG. 2D). According to alternative example embodiments consistent with the present invention, the adjustment mechanism providing this engaging and locking can be implemented using the illustrated ratchet-like ladder along the length of the extended portion of the main body 112. Alternative locking methods include threads or an elongated tube. By using a nonpermanent securing mechanism such as the illustrated ratchet-like ladder, the outer adjustment sleeve 116 can be advantageously readjusted.

FIGS. 2B and 2C illustrate example structures for the pin holder 130 and the pin 114. The pin holder 130 includes an aperture 130a for securing therein the pin 114 of FIG. 2C. The cam-like surface of the pin holder 130 is depicted as 130b. The pin 114 of FIG. 2C is expanded to show the bulb surface 114a for engaging and expanding the end 118c of the lock 118 (FIG. 2E), the tip 114b for incising the body wall, and the shaft 114c that enters the port 112b of the main body 112 (FIG. 2A).

The lock 118 of FIG. 2E and the outer adjustment sleeve 116 of FIG. 2D further show one of the interlocking sleeve/lock mechanisms. The lock 118 includes a pliable or flexible end with partially separable members 118c that, in response to receiving the bulb portion 114a of the pin 114 (FIG. 2C), are forced outwardly to mate protrusions 118d into apertures 116a of the sleeve 116.

These various components of FIGS. 2A–2F can be manufactured in a number of different ways including, for instance, via molded plastics (e.g., propylene).

Figure 3A:
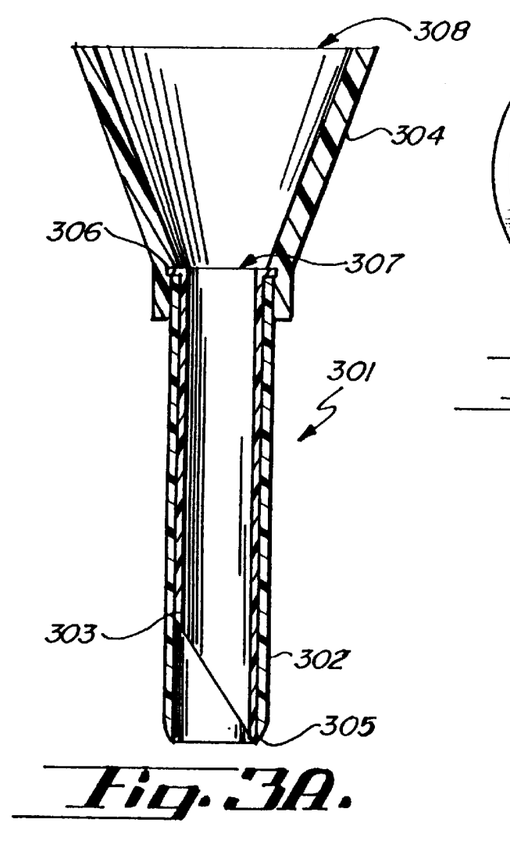
FIG. 3A is a side view of an outer cannula and an inner seal of an example surgical tool according to the present invention.

Referring now to FIG. 3A, an alternative surgical instrument 301 consists of an elongated rigid tube 302 in which a flexible tube or sleeve 303 is placed within a hollow channel located within the rigid tube 302. The flexible tube or sleeve 303 is supported on the rigid tube 302 using a weld 305 attaching the bottom of the tube to the side wall. The flexible tube is also supported with some overlap 306 at the point at which the rigid tube 302 mates with an entrance receptacle 304 as it attaches to the upper end of the rigid tube 302. The receptacle 304 is a funnel shaped device that has a wide opening 308 and a narrow opening 307 for mating with the rigid tube 302. This funnel structure is useful in guiding the insertion of external instruments into the rigid tube 302 and flexible tube 303 by permitting the funnel structure to guide the instruments towards the center of the rigid and flexible tubes.

In one embodiment, the flexible tube 303 is constructed of a slippery polyurethane or Teflon-like material to permit the easy passage of an external instrument through the sleeve to exit the rigid tube 302 at its first end 306. The flexible tube 303 has a slippery, plastic, polyurethane-like material to provide the required elasticity that allows the flexible tube 303 to be compressed under pressure and to close the opening of the inner channel formed within the flexible tube 303.

When in use for laparoscopic surgery, the rigid tube 302 is inserted within a small hole within the body cavity. The small hole within the body cavity can be sized to match the outer diameter of the rigid tube 302. The body cavity is generally pressurized using an inert gas, such as $CO_2$, such that the internal pressure within the body cavity is greater than the outside air. As such, when the rigid tube 302 is inserted within the pressurized body cavity, this pressurization enters the rigid tube at its first end 306 compressing the flexible tube 303 upwards. Because the flexible tube is attached using the weld 305, the flexible tube gathers and compresses, closing the opening of the inner channel thus preventing the escape of the pressurized gas from inside the body cavity.

When in this configuration, a surgical instrument can be inserted through receptacle 304, as it is passed through the opening 308 of receptacle 304 and to enter within the inner channel of the now collapsed flexible tube 303. As the instrument is inserted through the flexible tube, the flexible tube will conform around the external instrument, thus permitting the instrument to pass through both the flexible tube 303 and exit the rigid tube 302. At the same time, the pressurization is present within the rigid tube's first end 306. The pressurization continues to press the flexible tube against the surfaces of the external instrument as it passes through the inner channel, thus maintaining a within the inner channel. The external instrument can now be used to perform surgical procedures within the body cavity.

As the external instrument is removed, it passes back through the inner channel of the flexible tube. Pressurization from within the body cavity maintains the collapsed structure of the flexible tube, thus maintaining the seal of the inner channel around the instrument until it is closed when the instrument is completely removed.

Figure 3B:
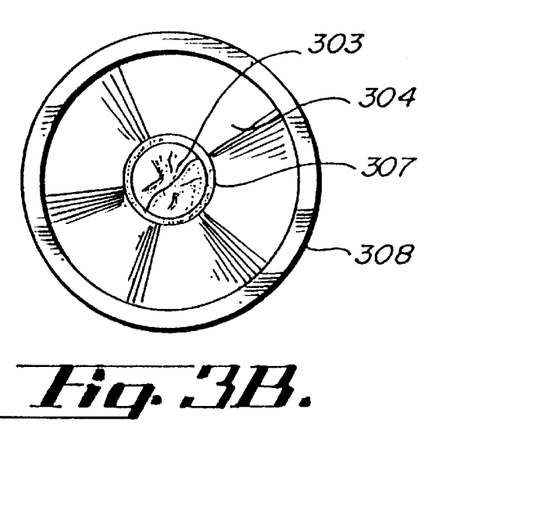
FIG. 3B is an end view according to the present invention of the cannula with its inner seal of the example surgical tool of FIG. 3A.

Referring to FIG. 3B, an end view of the surgical instrument looking down towards the top of the receptacle is shown. The outer edge 308 shows the outer dimension of the receptacle which funnels down towards the mating surface between the receptacle and the rigid tube 302 (FIG. 3A). The flexible tube 303 is depicted in its closed position as the flexible tube 303 is gathered up to close the opening within the inner channel formed within 307. While an external instrument is inserted down through the center of the structure, the flexible tube 303 conforms to the shape and surface of the external instrument.

Figure 3C:
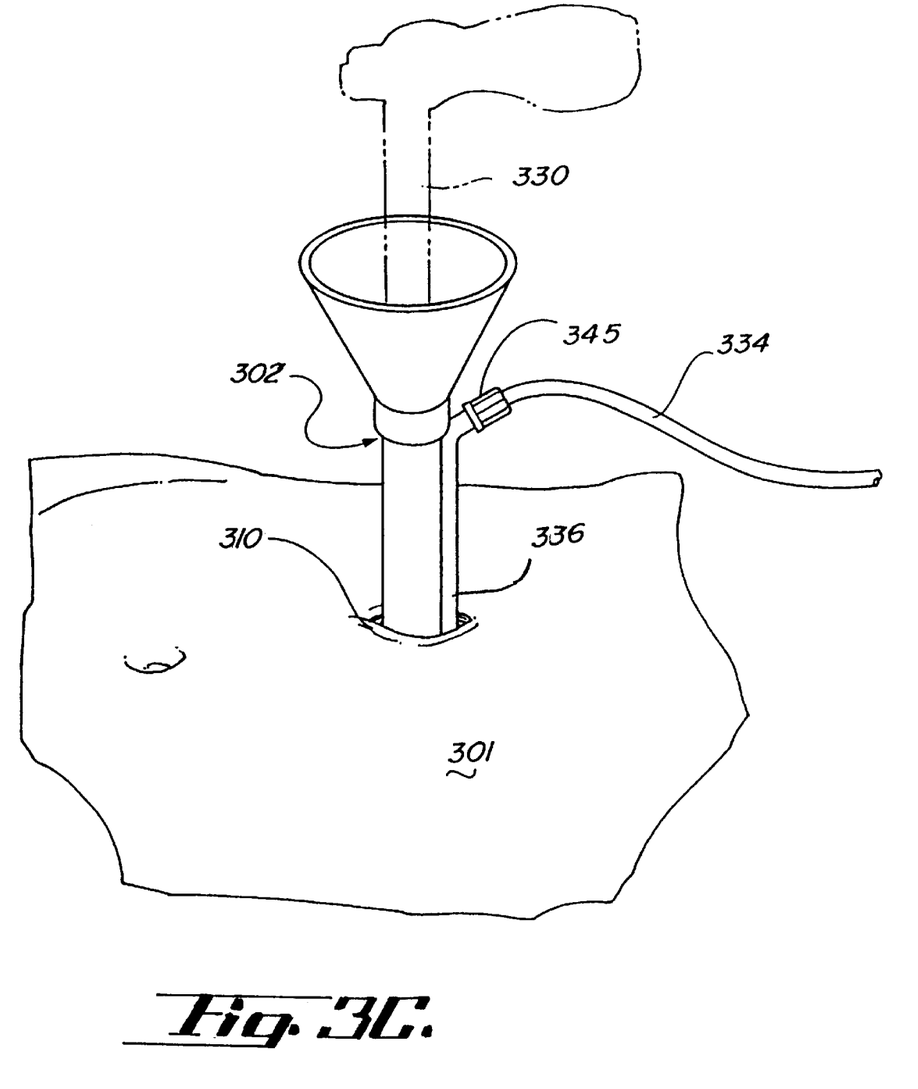
FIG. 3C is a perspective view showing how a surgical instrument, can be inserted through the cannula and its inner seal while maintaining a closed seal within the cannula, also according to the present invention.

Referring to FIG. 3C, an embodiment of the present invention is shown in use where a cannula structure 302 is inserted within a body cavity 301 at an incision 310. A surgical instrument 330 is passed through the center of cannula 302 through the inner channel of the flexible tube (not shown in FIG. 3C) that seals the opening through the cannula structure 302. In this particular embodiment, an additional channel structure 334 has been added which permits the supply of an inert gas to be placed within the body cavity 301. This structure 334 can be an inert gas line that comes from an external source connected to a valve structure 345 and that allows the gas supply to be turned on and off. In one example embodiment, this valve structure 345 is made part of the receptacle housing. This structure 334 is also connected to a secondary tube 336 that runs parallel to the rigid tube 302 of the cannula with an opening near the first end of the rigid tube 302 permitting the gas to enter within the body cavity 301 on the far end side and, providing the pressurization within the body cavity needed to close the inner channel of the flexible tube. This supply of gas can be made part of the canal as described herein or can be made as a separate structure inserted in the body at some other location.

The gas supply, as described and illustrated in connection with FIGS. 3A–3C, can be similarly implemented in connection with the structure shown in FIGS. 1A–1C, with a channel for the gas running inside or outside the tools main wall.

The above specification, examples and data provide a complete description of the manufacture and use of the composition of the invention. Since many embodiments of the invention can be made without departing from the spirit and scope of the invention, the invention resides in the claims hereinafter appended.

I claim:

1. An apparatus for inserting through a body layer and into a body cavity for surgical procedures, comprising:

an elongated member including an entry port, a hollow channel defining an opening, and an extended portion, the extended portion configured and arranged to stabilize a end of the apparatus above the body layer; and a flexible sleeve located within the hollow channel and having a lower end attached at least one area of and adjacent a bottom end of the extended portion of the elongated member and configured and arranged to close the opening in response to pressure received through a port adjacent said at least one area and defined by a majority of the peripheral respective outer and inner surfaces of the flexible sleeve and the surrounding elongated member at the bottom end of the extended portion and from within the body cavity.

2. An apparatus, according to claim 1, wherein the flexible sleeve is constructed and arranged to permit an external instrument to pass through the channel while maintaining the channel closed due to pressurization between the sleeve and an inner surface of the member.

3. An apparatus, according to claim 2, wherein the flexible sleeve has a first end supported near the entry port.

4. An apparatus, according to claim 3, further including a flexible sleeve lock that is constructed and arranged to provide another entry port that is aligned with the first-indicated entry port and to secure the first end of the flexible sleeve.

5. An apparatus, according to claim 4, wherein the first end of the flexible sleeve is secured adjacent the extended portion of the elongated member.

6. An apparatus, according to claim 5, further including a gas supply channel running along the elongated member arranged to provide a path outside of the flexible sleeve that passes an externally-supplied gas to the body cavity.

7. An apparatus, according to claim 6, wherein the extended portion includes a portion of the gas supply channel.

8. An apparatus, according to claim 1, further including an elongated pin arrangement constructed and arranged to lock within the elongated member and to puncture or pierce the body layer.

9. An apparatus, according to claim 8, wherein the elongated pin arrangement is constructed and arranged to extend adjustably along the elongated member.

10. An apparatus, according to claim 8, further including a sleeve arranged to receive the elongated member and to adjust the extent to which the elongated pin arrangement extends from the elongated member.

11. An apparatus for inserting through a body layer and into a body cavity for surgical procedures, comprising:

an elongated rigid tube including an entry port, a hollow channel defining an opening, an extended portion configured and arranged to stabilize an upper end of the apparatus above the body layer, and an adjustable member configured and arranged to adjust a lower end of the apparatus relative to the upper end; and a flexible sleeve located within the hollow channel and having a lower end attached to the elongated rigid tube at an attachment area defining less than a majority of the periphery of the elongated rigid tube, the attachment area being adjacent a bottom end of the elongated rigid tube, wherein the flexible sleeve is configured and arranged to compress under pressure received from within the body cavity and passing between the flexible sleeve and the elongated rigid tube to close the opening.

12. An apparatus, according to claim 11, further including means for securing an upper end of the flexible sleeve.

13. An apparatus, according to claim 11, further including means for supplying gas along the extended portion and into the body cavity.

14. An apparatus, according to claim 11, further including locking-piercing means for locking within the extended portion and piercing the body layer.

15. An apparatus, according to claim 14, further including a cam adapted to set the locking-piercing means.

16. An apparatus, according to claim 14, further including means for adjusting the position of an end of the elongated pin arrangement along with the length of the elongated tube.

17. A method for accessing through a body layer and into a body cavity for surgical procedures involving prestige in the body cavity, comprising:

providing a tool including an entry port, a hollow channel and an extended portion and a flexible sleeve within the hollow channel;

inserting the tool into the body layer and placing an upper part of the extended portion on the body layer with tile entry port above the body layer;

placing an instrument within the channel and within the flexible sleeve while the sleeve is secured near a bottom end of the extended portion, and receiving pressure from the body cavity through at least one port defined by a majority of the outer periphery of the flexible sleeve and a corresponding inner surface of the extended portion surrounding the flexible sleeve, to conform the flexible sleeve around the instrument while the instrument is within the channel, and permitting the flexible sleeve to close upon itself while no instrument is within the channel.

18. A method for accessing through a body layer and into a body cavity for surgical procedures, according to claim 17, further including adjusting the channel before inserting the tool.

19. An apparatus for use in an internal surgical procedure on a body, the procedure involving pressurization in a cavity of the body, comprising:

a platform adapted to rest the apparatus on the body, an adjustable elongated section for setting a lower end of the apparatus relative to the platform, and a hollow channel within the adjustable elongated section, and a flexible sleeve located within the hollow channel and adapted for receiving a surgical instrument while the sleeve is secured near a bottom and of the elongated section, the flexible sleeve being sufficiently elastic to close the hollow channel in response to pressurization received from within the body cavity through at least one port defined by a majority of the outer periphery of the flexible sleeve and a corresponding inner surface of the elongated section surrounding the flexible sleeve, to conform the flexible sleeve around the surgical instrument.

20. An apparatus for use in an internal surgical procedure on a body, according to claim 19, wherein the adjustable elongated section includes an inner rigid tube and an outer-sleeve arranged to be adjustably set at any of a plurality of positions along the inner rigid tube for setting the lower end of the apparatus relative to the platform.

21. An apparatus for use in an internal surgical procedure on a body, the procedure involving pressurization in a cavity of the body, comprising:

means for resting the device on the body;

elongated means secured to the resting means having at least one inner surface defining a hollow channel; and flexible means for scaling located within and secured near a bottom end of the hollow channel, forming an inner channel, and for closing the inner channel in response to pressurization received from within the body cavity through at least one port defined by a majority of the outer periphery of the flexible means and a corresponding inner surface of the elongated means surrounding the flexible sleeve to conform the flexible means around the surgical instrument.

* * * * *